United States Patent [19]

Erceg

[11] 4,245,633
[45] Jan. 20, 1981

[54] PEEP PROVIDING CIRCUIT FOR ANESTHESIA SYSTEMS

[76] Inventor: Graham W. Erceg, 4716 N. Stratford Oaks, Macon, Ga. 31204

[21] Appl. No.: 8,117

[22] Filed: Jan. 31, 1979

[51] Int. Cl.³ ............................................ A61M 16/00
[52] U.S. Cl. ............................ 128/205.17; 128/205.24
[58] Field of Search ..................... 128/145.5–145.8, 128/188, 204.25, 205.13, 205.15, 205.16, 205.17, 205.24

[56] References Cited

U.S. PATENT DOCUMENTS

| | | | |
|---|---|---|---|
| 2,841,142 | 7/1958 | Hay | 128/188 |
| 3,028,873 | 4/1962 | Kindred | 128/188 X |
| 3,621,842 | 7/1969 | Manley | 128/204.25 |
| 3,856,051 | 12/1974 | Bain | 138/114 |
| 3,916,888 | 11/1975 | Buck et al. | 128/204.21 |
| 3,933,171 | 1/1976 | Hay | 128/188 X |
| 4,026,284 | 5/1977 | Boehringer | 128/188 |
| 4,051,847 | 10/1977 | Henkin | 128/188 X |

Primary Examiner—Henry J. Recla
Attorney, Agent, or Firm—Diller, Ramik & Wight

[57] ABSTRACT

A system for conducting gas flow from anesthetic and respirator machines to a medical patient when the patient inhales, and for conducting reverse gas flow, when the patient exhales, through a PEEP valve thereby to provide the positive end-expiratory pressure (PEEP) effect for a medical patient interoperatively.

13 Claims, 3 Drawing Figures

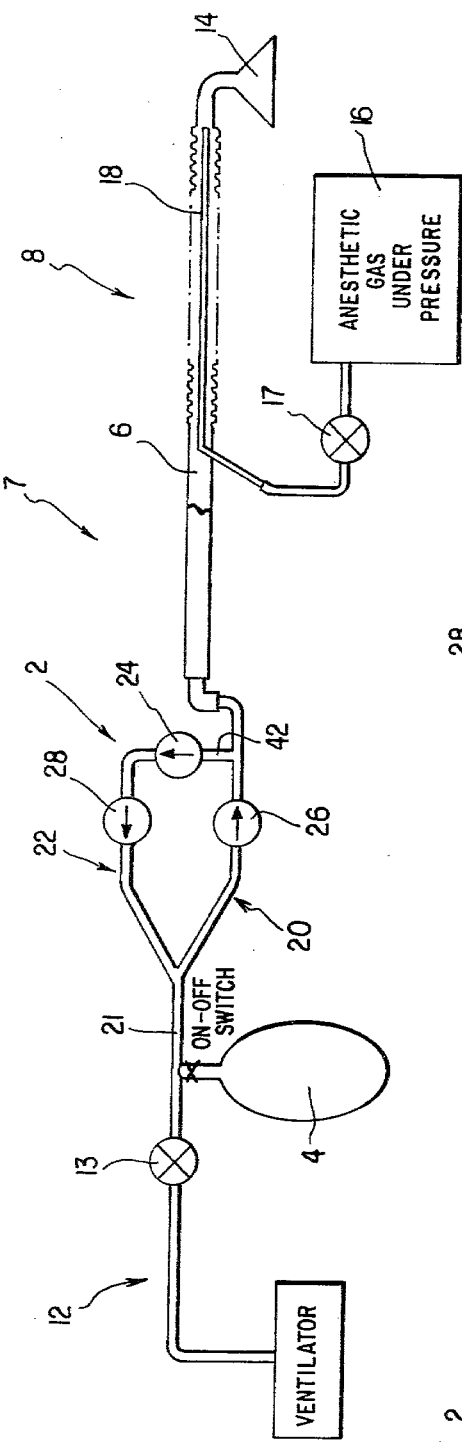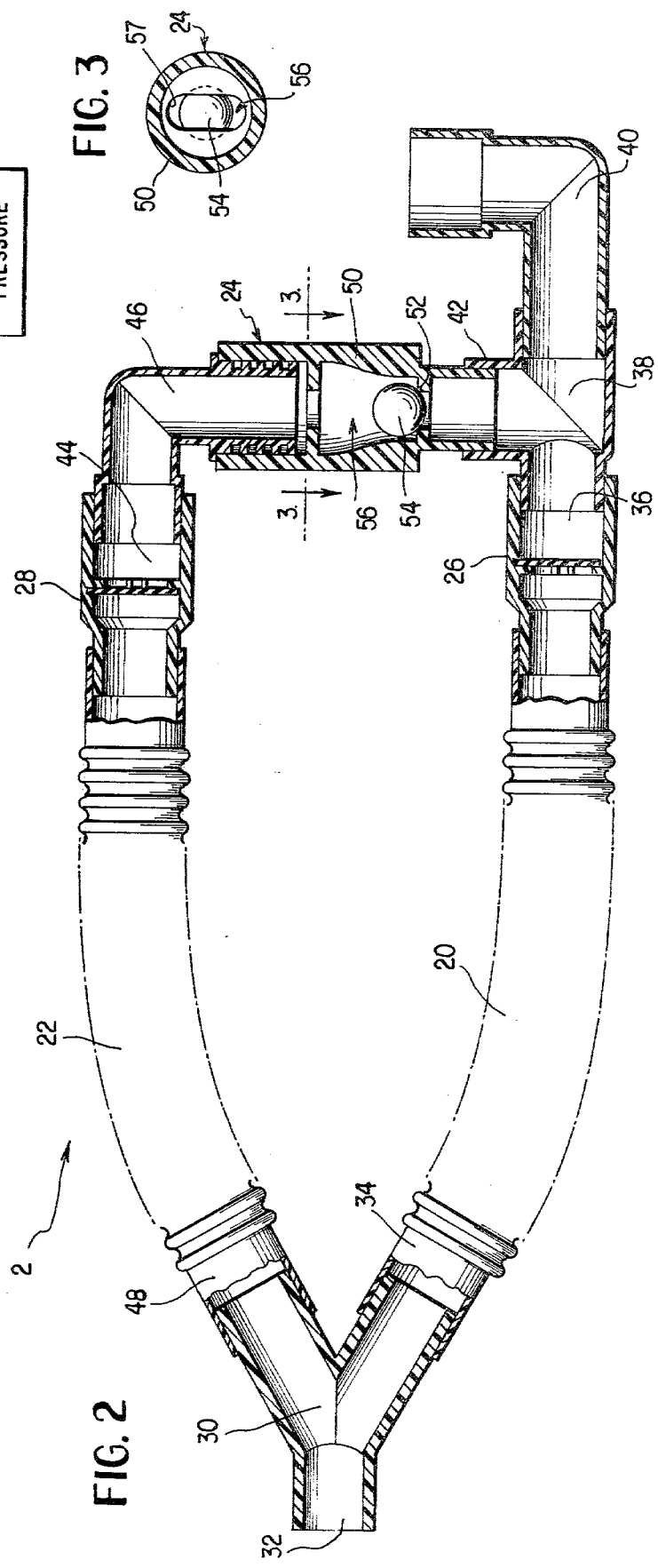

PEEP PROVIDING CIRCUIT FOR ANESTHESIA SYSTEMS

BACKGROUND OF THE INVENTION

Devices for providing positive end-expiratory pressure (PEEP) have been successfully used in the treatment of medical patients having respiratory disorders, such as adult respiratory distress syndrome. The PEEP is provided by restricting the flow of gases exhaled by the patient so that such gases must be exhaled against resistance. In this way the gases exhaled by the patient are subjected to positive pressure resisting exhalation which in turn pressurizes the patient's lungs.

The pressurization of a patient's lungs has been found to be beneficial in treating some respiratory and cardiovascular disorders. It has been found that the provision of PEEP for a medical patient may lower his blood pressure. However, the administering of PEEP interoperatively has not been generally practicable, particularly with the Baincircuit which is described fully hereinafter, due to its interference with anesthesia machines utilized in surgical procedures.

Attempts have been made to provide PEEP for patients being anesthetized but the devices used for providing such PEEP have been found to be awkward. One such device is disclosed in the Wu and Turndorf article found on pages 677 and 678 of *Anesthesiology* V 43, No. 6, Dec. 1975.

The Turndorf device comprises a conduit through which the patient exhales. A distal end of the conduit terminates in a substantially vertically disposed outlet which is covered by a substantially horizontally disposed valve leaflet. The valve leaflet completely closes off the outlet but is easily pushed out of seating engagement therewith by the gases exhaled by the patient. The requisite flow restriction for PEEP devices is provided by a biasing means which tends to seat the leaflet against the outlet. In the Turndorf device the biasing means comprises a vertically disposed water filled column having a flexible membrane bottom which abuts against the valve leaflet. With this device the gases exhaled by the patient must be of sufficient pressure to overcome the weight of the water in the column biasing the leaflet closed in order to unseat the leaflet and let the gases escape through the outlet.

However, the Turndorf device is prone to leakage and rupture of the flexible membrane bottom. Although such leakage or the like constitutes no threat to the patient, it does result in failure to provide the PEEP effect.

Other attempts have been made to provide PEEP in anesthesia circuits, such as those described by Weeks and Comer in their article beginning at page 578 of *Anesthesia and Analgesia* Vol. 56, No. 4, July–Aug., 1977. Weeks and Comer endeavored to adapt the Boehringer Laboratories PEEP valve for use with commonly used anesthesia machines. The Boehringer valve is a unidirectional or check valve of the ball type. This valve utilizes a weighted ball which normally blocks flow through the valve when the valve is properly positioned in vertical alignment. In this position the effect of gravity against the ball provides the necessary biasing means for PEEP. However, although this valve is not prone to failure, unless it is malpositioned, it subjects the anesthesia machine with which it is used to backpressure. This backpressure must be compensated for by modifying the anesthesia machine. Such need for modification of anesthesia machines also prevents the general applicablility of PEEP for interoperative procedures.

A further drawback in providing PEEP interoperatively is that no adaptation has been made for providing PEEP in conjunction with the extensively used Bain breathing system or circuit.

The Bain breathing circuit, disclosed in U.S. Pat. No. 3,856,051 and in his article of July 1972 in *Canadian Anesthetists Society Journal* beginning at page 426, comprises an extension conduit disposed between a reservoir bag of an anesthesia machine and a mask angle. This conduit, which was initially used as a modification for the Mapleson rebreathing system, is used to remove the reservoir bag, a pop-off valve and the like from the immediate vicinity of surgical procedures. This allows the placing of the reservoir bag in a location where it will not be obtrusive during the surgical procedure.

The extension conduit of the Bain circuit is a single limb circuit which conducts gases inhaled and exhaled by the patient to and from the patient and the respirator machine or apparatus. Co-extending longitudinally within the extension conduit is a fresh gas conduit which supplies anesthetic gas to the mask angle from the anesthesia machine.

Dur to the many advantages provided by the Bain circuit it has been widely accepted and is now in general use for surgical procedures. However, since the Bain circuit comprises a single limb for conducting inhaled and exhaled gases, positive end-expiratory pressures devices have not been utilized therewith due to their unidirection flow characteristics. Simply stated, if a unidirectional valve, which provides PEEP, were disposed within the Bain circuit, it would block the flow of gases from the respirator to the patient. Therefore, there has not existed until the present invention a means for providing PEEP in conjunction with this prevalently utilized anesthetic circuit.

BRIEF SUMMARY OF THE INVENTION

This invention relates to a circuit for providing positive end-expiratory pressure, and in particular to a circuit for providing such PEEP interoperatively in conjunction with anesthetic systems. The invention disclosed herein evisages the effective use of the Boehringer Laboratories PEEP valves or equivalents in conjunction with existing anesthetic systems, and is particularly suited for use with the Bain breathing circuit.

The PEEP providing circuit of this invention generally comprises an assembly which is adapted to be disposed between the reservoir bag and the breathing conduit of an anesthetic system. This system is provided with separate inspiratory and expiratory conduits in order to allow inhalation and exhalation respectively, to proceed therethrough. These conduits are interconnected at an end adjacent the reservoir bag to terminate in a common opening which is in communication with the reservoir bag. Another end of the insiratory conduit is attached to a dual path fitting, such as an inverted T-fitting. The inspiratory conduit is substantially horizontally disposed and is attached to one end of one branch of the inverted T-fitting which is likewise horizontally disposed. Another end of this branch is attached to the breathing conduit of the anesthetic system. A further branch of the dual path fitting is positioned in substantially vertical disposition. A PEEP valve, for example a Boehringer Laboratories valve, is coupled at one end to the other path of the dual path fitting and is also vertically disposed. The other end of the PEEP valve is adapted for connection with the other end of the expiratory conduit.

A unidirectional or check valve is disposed between the two ends of each of the inspiratory and expiratory conduits. These valves assure only flow from the common opening to the dual path fitting through the inspiratory conduit and flow from the dual path fitting to the common opening through the expiratory conduit. In this way, when the patient breathes, the gas flow to him is undisturbed when he inhales, and when he exhales the gas flow is directed through the PEEP valve thereby to provide the positive end-expiratory pressure effect.

This breathing circuit is easily adapted to be used in conjunction with conventionally used anesthetic systems, and is very well suited to be used with the Bain rebreathing circuit.

BRIEF DESCRIPTION OF THE DRAWINGS

FIG. 1 is a schematic view of an anesthetic system incorporating an embodiment of the present invention;

FIG. 2 is a fragmentary side elevational view of the breathing circuit of the present invention; and FIG. 3 is a sectional view taken along line 3—3 of FIG. 2.

DETAILED DESCRIPTION OF INVENTION

A preferred embodiment of the invention is shown in FIG. 1 wherein a breathing circuit or PEEP providing circuit 2 is disposed between a reservoir or respirator bag 4 and a flexible extension conduit 6 of an anesthetic system 7. The anesthetic system 7 is a conventional system which includes a Bain rebreathing circuit 8. The Bain rebreathing circuit 8 as described hereinbefore comprises the flexible extension conduit 6 which normally interconnects a positive pressure source 12, such as a respirator, ventilator or machine, and a patient associated mask angle or face mask 14. Normally with the Bain system fresh anesthesia is supplied from an anesthetic machine 16 through a fresh gas conduit 18 to the mask angle 14. The mask angle 14 is attached to the medical patient's face for providing direct communication of gases with the patient's oral and/or nasal passages, and can be exchanged for an endotracheal tube or the like. When the patient exhales, the gases expelled by him travel from the face mask 14 through the conduit 6 back to the reservoir bag 4 or through the exhaust valve 13.

In this system, as is conventional, the expansion and contraction of the respirator bag 4 are used as visual indicators of the patient's breathing for the anesthesiologist and as an indicator of the patient's lung's tidal volume. The anesthesiologist uses the visual indications provided by the reservoir bag 4 to tailor the amount of gases supplied to the patient. For example, if the reservoir bag 4 fails to expand to a predetermined extent when the patient exhales, the anesthesiologist will become apprised that the full tidal volume of the patient's lungs has not been realized and he will then increase the gas flow from the reservoir bag 4 and/or the anesthetic machine 16 by adjusting their respective regulator valves 13 and 17. Conversely, if the reservoir bag 4 fails to collapse sufficiently the anesthesiologist will note that the patient's tidal volume has been exceeded and he will decrease the amount of gas flow administered to the patient by the respirator 12 and/or the anesthetic machine 16. Therefore, it is of fundamental importance that any device for providing positive end-expiratory (PEEP) for a medical patient be disposed between the patient and the reservoir bag 4. If this arrangement were not adhered to the gas flow from the patient would simply be diverted to the reservoir bag 4 unitl completely filled, at which time the gases would flow through the PEEP circuit or device 2 to provide PEEP for the patient only during a limited portion of his expiratory cycle. It is for this reason that the PEEP circuit 2 of the present invention is disposed between the extension conduit 6 and the reservoir bag 4.

The PEEP circuit 2 shown in FIG. 2 of the present invention generally comprises inspiratory conduit means or an inspiratory conduit 20 which transfers gases from a respirator conduit 21, leading to the respirator 12, to the extension conduit 6. The PEEP circuit 2 also includes expiratory conduit means or an expiratory conduit 22, which transfers gas flow from the extension conduit 6 back to the respirator conduit 21, and reverse flow resisting means or a unidirectional PEEP providing valve 24, which is disposed between the conduit 6 and the expiratory conduit 22. The inspiratory conduit 20 includes valve means or a valve 26 which assures that gas flow returning to the respirator 12 is prevented from entering the inspiratory conduit 20 and is instead routed through the PEEP valve or PEEP providing valve 24 to the expiratory conduit 22. The expiratory conduit 22 similarly may be provided with unidirectional valve means or a valve 28 which prevents gas flow from the respirator conduit 21 to pass therethrough.

The breathing circuit 2 of FIG. 2 is coupled with the respirator conduit 21 (FIG. 1) by a Y-shaped connector or coupling member 30 which terminates in a common opening 32. When the patient inhales gas flow enters the opening 32 and travels therethrough to an inlet end portion 34 of the inspiratory conduit 20. The gas flow then proceeds through the inspiratory conduit 20, through the unidirectional valve 26 and discharges from an outlet end portion 36 to a dual path, inverted T-shaped fitting 38. The gas flow then passes from the fitting 38 to the breathing conduit 6 (FIG. 1) via any suitable coupling means, such as an elbow connector 40. This gas flow is prevented from traveling through the expiratory conduit 22 by the valve 28 (or by the unidirectional PEEP valve 24 when the valve 28 is not employed).

When the patient exhales, gas flows through the breathing conduit 6 to the connector 40. This gas flow then passes into the dual path fitting 38. Since the unidirectional valve 26 is located adjacent the fitting 38 the gas is prevented from entering the inspiratory conduit 20 and is diverted upwardly through a second path via a stem 42 of the inverted T-shape fitting 38. This assures that the gases exhaled by the patient pass through the PEEP valve 24. The exhaled gases then flow from the expiratory valve means or PEEP valve 24 to an inlet end portion 44 of the expiratory conduit 22 and therethrough to discharge from an outlet end portion 48 into the fitting 30. These gases are then conducted through the coupling member 30 and the common opening 32 to the respiratory conduit 21.

A connector 46 and the stem 42 are provided in order to maintain the PEEP valve 24 in substantially vertical disposition while allowing the conduits 20 and 22 to assume a generally horizontal position.

The PEEP valve 24 is gravity biased in order to provide flow restricting means which acts against the flow of gases exhaled thereto by the patient. The flow restricting or resisting means 24 shown herein consists of a commercially available Boehringer Laboratories positive expiratory pressure valve, Model 4801, and can be replaced by any other suitably biases unidirectional valve. For clarity, however, the Boehringer Laboratories valve will be described herein as being the PEEP valve 24 employed in the present invention. This flow restricting means 24 comprises a unidirectional valve of the ball cock type which includes a valve body 50, a valve seat 52 and a checking ball 54. The valve body 50 has a passage 56 extending longitudinally therethrough, through which the exhaled gases pass. As shown in the vertical position, the valve seat 52 is disposed adjacent the bottom of the valve passage 56. The checking valve 24, in this position, is a normally closed valve. In order for gas flow to proceed through the valve 24, the gases must be of a sufficient pressure to lift the ball 54 out of seating engagement with the valve seat 52. This ball 54 is biased against the valve seat 52 by a predetermined amount so that in order to unseat the ball 54 the pressure of the gases expelled by the patient must exceed the predetermined biasing force. The biasing means of this valve is the effect of gravity imposed upon the valve ball 54. In this way biasing forces against the gas flow can be established accurately by using a precisely weighted ball. The Boehringer valve Model 4801, for example, utilizes a ball which has a weight corresponding to that of a 5 centimeter volume of water. Therefore, in order for a patient to exhale through this particular system, he must expel the expiratory gases at a pressure greater than that produced by 5 cm of water.

Due to the biasing effect of gravity on the ball 54, the valve 24 must be maintained in substantially vertical position in order to provide positive end-expiratory pressure. However, if the valve 24 becomes malpositioned, it simply will fail to provide PEEP but it will not block flow therethrough. Therefore, if malpositioned the valve 24 would not present any threat to the patient as he would be able to exhale freely therethrough. As is apparent from FIG. 2, if the valve 24 were, for example, disposed in a generally horizontal position, the ball 54 would roll away from the valve seat 52 and thereby unseat itself. From the view shown in FIG. 3, it can be seen that the valve passage 56 extending through the valve body 50 of the PEEP valve 24 has an elongated part 57 which is longer than the diameter of the ball 54. This is to insure that the passage 56 inadvertently cannot become blocked by the ball 54 if the valve 24 is malpositioned.

Again referring to FIG. 1, the function of the PEEP providing breathing circuit 2 of the present invention will be described herewith in conjunction with the Bain rebreathing circuit 8. The mask angle 14 is affixed to the patient's face or tracheal passage for directing gas flow to and from his lungs. This mixture is conducted by the respiratory conduit 21 to the breathing circuit 2. The gases then flow through the inspiratory conduit 20 to the extension conduit 6 of the Bain circuit 8. This gas flow is prevented from passing through the expiratroy conduit 22 of the breathing circuit 2 by the unidirectional valve 28 (or by the PEEP valve 24 in the absence of the valve 28). The breathing mixture then proceeds through the conduit 6 and is commingled with fresh anesthetic gas, supplied by the anesthetic machine 16 through the conduit 18, adjacent the mask angle 14. These commingled gases are then directed through the mask angle 14 to the patient's lungs. Upon exhaling by the patient, the gas flow is reversed. The reverse gas flow then flows from the patient's lungs through the mask angle 14 to the conduit 6 and therethrough to the breathing circuit 2. The unidirectional valve 26 prevents this reverse flow from passing through the inspiratory conduit 20. The reverse gas flow is thereby forced to travel through the stem 42 to the PEEP valve 24. Due to the biasing of the PEEP valve 24, the patient must force the gases out of his lungs when he exhales in order to pressurize the gases sufficiently to counteract the biasing gravity force of the ball 54 and allow the gases to pass therethrough to the expiratory conduit 22. This reverse gas flow then proceeds through the conduit 22 to the respirator 12 via the conduit 21 and the exhaled gas is released through exhaust valve 13. The procedure is, of course, repeated each time the patient inhales and exhales.

The biasing of the ball 54 and its concommitant effect of causing the patient's lungs to force out the expelled gases causes the patient's lungs to be pressurized. This form of pressurizing the lungs is known as providing PEEP (positive end-expiratory pressure) for the patient. The provision of such PEEP for a medical patient is recognized in the medical field as being beneficial in the treatment of respiratory disorders and for lowering blood pressure. However, the provision of PEEP interoperatively in conjunction with anesthetic systems was not generally practicable. This need in the medical field is, however, overcome by the PEEP providing circuit 2 described herein, in its preferred embodiment in conjunction with the Bain rebreathing circuit 8.

While preferred forms and arrangements of parts have been shown in illustrating the invention, it is to be clearly understood that various changes in details and arrangement of parts may be made without departing from the scope and spirit of this disclosure.

I claim:

1. A breathing circuit for providing positive end-expiratory pressure for a medical patient, said circuit comprising in combination:

inspiratory conduit means for conducting flow of gas to a patient when the patient inhales, said inspiratory conduit means having inlet and outlet end portions adapted for connection to a source of positive pressure and a patient, respectively;

first unidirectional valve means disposed between said end portions of said inspiratory conduit means for precluding reverse flow of gas in said inspiratory means upstream of said first valve means when a patient exhales;

unidirectional expiratory valve means disposed between said first valve means and said outlet end portion for discharging reverse flow of gas through said expiratory valve means when a patient exhales;

said expiratory valve means being biased for providing fixed predetermined positive pressure resistance above that of the positive pressure source against reverse flow of gas downstream of said first unidirectional valve means thereby providing said positive end-expiratory pressure; and said circuit includes expiratory conduit means having inlet and outlet end portions, said expiratory inlet end portion being interconnected with said expiratory outlet end portion being interconnected with said inlet end portion of said inspiratory conduit means to provide a common opening whereby reverse flow of gas is conducted from said expiratory valve means to said common opening.

2. The breathing circuit as defined in claim 1 wherein said expiratory valve means is biased by the effect of gravity.

3. The breathing circuit as defined in claim 1 wherein said expiratory valve means is biased by the effect of gravity and is disposed substantially vertically.

4. A breathing circuit as defined in claim 1 wherein said circuit includes third unidirectional valve means disposed between said expiratory valve means and said inlet end portion of said expiratory conduit means for preventing gas flow other than said reverse flow of gas from passing through said expiratory conduit means.

5. The breathing circuit as defined in claim 4 wherein said expiratory valve means is biased by the effect of gravity and is disposed substantially vertically.

6. The breathing cirucit as defined in claim 1 wherein said expiratory valve means is biased by the effect of gravity and is disposed substantially vertically.

7. In a system for ventilating a medical patient including means for transferring gas to and from a patient, ventilating means for producing positive pressure for ventilating the patient, conduit means for interconnecting said gas transferring means and said ventilating means, and a reservoir bag communicating with said conduit means; an improvement to said system of a breathing circuit for providing positive end-expiratory pressure for the medical patient comprising in combination:

inspiratory conduit means having inlet and outlet end portions disposed between said ventilating means and said conduit means, said inlet end portion being interconnected with said ventilating means and said outlet end portion being interconnected with said conduit means, said inspiratory conduit means conducting gas flow from said ventilating means to said conduit means when the patient inhales;

first unidirectional valve means disposed between said end portions of said inspiratory conduit means for precluding reverse gas flow through said inspiratory conduit means upstream of said first valve means when the patient exhales;

unidirectional expiratory valve means disposed between said first valve means and said outlet end portion for discharging reverse gas flow through said expiratory valve means when the patient exhales;

said expiratory valve means being biased for providing fixed predetermined positive pressure resistance above that of said ventilating apparatus against reverse gas flow downstream of said first unidirectional means thereby providing said positive end-expiratory pressure; and expiratory conduit means having one end thereof in communication with said expiratory valve means and the other end thereof in communication with said inlet portion thereby to conduct reverse gas flow therethrough from said expiratory valve means toward said ventilating means.

8. A system for ventilating a medical patient as defined in claim 7 wherein said inlet end portion of said inspiratory conduit and said other end of said expiratory conduit are interconnected to provide a common opening which is in communication with said ventilating means.

9. A system as defined in claim 8 wherein said expiratory conduit includes second unidirectional valve means disposed between said one end and said other end thereof for preventing said gas flow from preceding therethrough.

10. A system as defined in claim 7 wherein said expiratory valve means is biased by the effect of gravity.

11. A system as defined in claim 10 wherein expiratory valve means is disposed in substantially vertical position.

12. In a rebreathing anesthetic system of the Bain type which comprises a Bain attachment consisting of a length of light weight flexible tubing having one end adapted for patient connection by means of a mask angle or the like, an opposite end adapted to be connected to a reservoir bag, and fresh gas inflow conduit means extending into said flexible tubing and extending essentially coaxially therein for delivering fresh gas to the patient, and a reservoir bag connected to said opposite end of the tubing, the improvement which comprises a breathing circuit for providing positive end-expiratory pressure for a patient, said circuit including:

inspiratory conduit means disposed between said reservoir bag and said opposite end of the flexible tubing for conducting flow therethrough from said reservoir bag to said flexible tubing when the patient inhales, said inspiratory conduit means having inlet and outlet end portions, said inlet end portion being interconnected with said reservoir bag and said outlet end portion being interconnected with said flexible tubing;

unidirectional valve means disposed within said inspiratory conduit means for precluding reverse gas flow through said inspiratory conduit means when the patient exhales;

unidirectional expiratory valve means disposed between said unidirectional valve means and said outlet end portion of said inspiratory conduit means for conducting reverse flow therethrough, said expiratory valve means being biased to provide fixed predetermined positive pressure resistance against said reverse gas flow; and expiratory conduit means for conducting reverse flow therethrough from the patient to said reservoir bag, said expiratory conduit means having inlet and outlet end portions, said inlet end portion being interconnected with said expiratory valve means and said outlet end portion being interconnected with said inlet end portion of said inspiratory conduit.

13. The breathing system as defined in claim 12 wherein said expiratory valve means is gravity biased and disposed substantially vertically between said expiratory conduit means and said inspiratory conduit means.

* * * * *